United States Patent [19]

Tovey et al.

[11] Patent Number: 5,370,650
[45] Date of Patent: Dec. 6, 1994

[54] ARTICULATING MESH DEPLOYMENT APPARATUS

[75] Inventors: H. Jonathan Tovey, Milford; Paul Matula, Brookfield, both of Conn.

[73] Assignee: United States Surgical Corporation, Norwalk, Conn.

[21] Appl. No.: 81,857

[22] Filed: Jun. 22, 1993

Related U.S. Application Data

[63] Continuation of Ser. No. 840,457, Feb. 24, 1992, abandoned.

[51] Int. Cl.$^5$ .............................................. A61B 17/00
[52] U.S. Cl. ................... 606/151; 128/899; 623/11
[58] Field of Search ............ 606/1, 107–108, 606/113, 139, 144, 148, 151, 205, 207, 213, 215; 604/280, 281; 600/37; 128/899; 623/11, 15

[56] References Cited

U.S. PATENT DOCUMENTS

| | | |
|---|---|---|
| 460,940 | 10/1891 | Baugh . |
| 736,744 | 8/1903 | Kratzmueller ............ 606/113 |
| 870,021 | 11/1907 | Duffee ...................... 606/113 |
| 2,767,703 | 10/1956 | Nieburgs . |
| 3,525,339 | 8/1970 | Halligan . |
| 3,540,431 | 11/1970 | Mobin-Uddin ........... 128/899 |
| 3,811,446 | 5/1974 | Lerwick et al. . |
| 4,190,042 | 2/1980 | Sinnreich . |
| 4,425,908 | 1/1984 | Simon ................... 606/200 X |
| 4,557,255 | 12/1985 | Goodman . |
| 4,586,502 | 5/1986 | Bedi et al. . |
| 4,732,150 | 3/1988 | Keener, Jr. . |
| 4,744,364 | 5/1988 | Kensey . |
| 4,807,626 | 2/1989 | McGirr . |
| 4,832,055 | 5/1989 | Palestrant ............ 128/899 |
| 4,917,089 | 4/1990 | Sideris . |
| 4,955,889 | 9/1990 | Van Gent ................ 606/107 |
| 5,061,274 | 10/1991 | Kensey . |
| 5,064,435 | 11/1991 | Porter ................. 606/151 X |
| 5,080,088 | 1/1992 | LeVahn . |
| 5,116,357 | 5/1992 | Eberbach . |
| 5,122,155 | 6/1992 | Eberbach . |
| 5,141,515 | 8/1992 | Eberbach . |
| 5,147,374 | 9/1992 | Fernandez . |
| 5,176,692 | 1/1993 | Wilk et al. . |

FOREIGN PATENT DOCUMENTS 2567405  7/1984  France .

OTHER PUBLICATIONS

Surgical Laparoscopy & Endoscopy vol. 1, No. 3, pp. 151–155, Raven Press, Ltd. (1991).

*Primary Examiner*—Stephen C. Pellegrino
*Assistant Examiner*—J. A. Schmidt

[57] ABSTRACT

An apparatus is disclosed for positioning surgical implants adjacent to body tissue. The apparatus includes a delivery device having a support member positioned at the distal end of an elongated rod, and a surgical implant releasably secured to the support member. The invention also provides a method for positioning surgical implants adjacent to body tissue using the apparatus of the present invention.

12 Claims, 6 Drawing Sheets

ARTICULATING MESH DEPLOYMENT APPARATUS

This is a continuation of copending application Ser. No. 07/840,457, filed on Feb. 24, 1992, now abandoned.

BACKGROUND OF THE INVENTION

1. Field of the Invention

The present invention relates to an apparatus and method for positioning surgical implants adjacent to body tissue to facilitate the fastening of the implant to the body tissue.

2. Description of the Related Art

Hernias are abnormal protrusions of an organ or other body structure through a defect or natural opening in a covering membrane, muscle or bone. An inguinal hernia is a protrusion which makes its way through the abdomen in the inguinal (groin) region. Hernias may be divided into three general classes: direct inguinal hernia, indirect inguinal hernia and femoral hernia. In both a direct and indirect inguinal hernias, a part of the intestine may protrude through a defect (opening or tear) in the supporting abdominal wall to form a hernial sac. In a femoral hernia, a portion of the intestine is forced through the femoral ring into the femoral canal forming a hernial sac.

Hernia repair typically requires surgery which generally includes an incision in the groin ranging up to six inches in length. Several layers of the abdominal wall are generally separated to reach the herniated portions. During the procedure, the opening or tear in the abdominal wall is closed in a manner which resembles the tying of a sack at the neck. Often a surgical mesh is attached by sutures directly over the repaired hernia opening to provide a reinforcement to the opening.

Traditionally, such hernia repairs involved major invasive surgical procedures which often caused excessive trauma to the patient and necessitated unusually long post-operative recuperative periods. In addition, numerous complications, related directly or indirectly to the surgery often resulted, including bleeding, infection, testicular atrophy, organ damage, nerve damage, blood vessel damage, etc. Further, cutting through the numerous layers of tissue to obtain access to the herniated area often caused severe trauma to the patient. A detailed discussion of traditional hernia repair may be found in "Hernia Repair Without Disability, Second Edition", by Irving L. Lichtenstein. Such invasive surgical procedures have also been utilized in other areas of the body, including surgery on the gall bladder, appendix, lungs and the like.

To, avoid many of the previously stated risks and problems, the use of laparoscopic and endoscopic surgical procedures ave been relatively popular and have provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from a proximal end of the instrument.

In hernia surgery, as compared to gall bladder surgery, certain procedures and instruments are the same, and certain instrument requirements differ. For example, in hernia surgery a suitable mesh material is generally sutured over the opening in the tissue. Often, the mesh material is attached by sutures and left within the body to act as a reinforcing agent for tissue regrowth in the area of the surgery. Ore example of a mesh material currently utilized in hernia surgery includes a polypropylene material marketed by C. R. Bard under the trademark MARLEX. Another example of a mesh material is a tri-fluoroethylene material marketed by W. L. Gore & Associates, Newark, Delaware, under the trademark GCRE-TEX.

As noted, during conventional invasive surgical procedures, such mesh materials are manually placed over the defect in the abdominal wall and are often sutured within the surgical opening by conventional suturing techniques. However, with the advent of laparoscopic surgery the need for suitable mesh, mesh positioning and mesh attachment techniques through the relatively narrow endoscopic tubes or cannulas is clearly defined. Up to the present, such devices and techniques for mesh positioning have not yet been developed.

Heretofore, resilient umbrella-type devices or extractors have been provided to remove objects from body tissue. Exemplary of these devices is U.S. Pat. No. 4,557,255 to Goodman. Goodman discloses a purse-like surgical net which is operable for retrieving stones and the like from within the human body.

U.S. Pat. No. 4,190,042 to Sinnreich discloses a resilient surgical retractor which in an unstressed condition forms a hook-like appendage at the distal end of the retractor.

U.S. Pat. No. 4,586,502 to Bedi et al. discloses a surgical instrument for implanting an "H"-shaped fastener in body tissue and a method of applying fasteners to skin or other tissue in a surgical procedure as an alternative to suturing a wound or surgical incision.

However, there remains a need for an apparatus which facilitates the securing of surgical implants for endoscopic positioning of the implant adjacent to body tissue. In addition to the above apparatus, the present invention relates to a method for positioning surgical implants adjacent to body tissue for stapling.

SUMMARY OF THE INVENTION

The present invention relates to an apparatus for positioning surgical implants adjacent to body tissue, comprising a delivery device having a support member positioned at the distal end of an elongated rod and a surgical implant releasably secured to the support member. The present invention also provides a method for positioning surgical implants adjacent to body tissue, comprising securing a surgical implant to a delivery device by passing a securing device at least partially through the surgical implant and wrapping the securing device around the delivery device.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

In general, the object of the present invention is to endoscopically position a surgical implant adjacent to body tissue for attachment thereto. More particularly, the present invention is directed to an apparatus to position a surgical implant adjacent to herniated body tissue during hernia surgery. The surgical implant is then affixed to the body tissue by means of sutures, clips and/or staples.

The surgical implant may be an implantable sheet material configured in a variety of shapes or forms. For example, the implantable sheet material may be flat, ball-shaped, cylindrically or tubularly rolled, as well as any other configurations within the knowledge of those skilled in the art. In addition, the implantable sheet material may be a solid sheet, shown in FIG. 1, a mesh-like sheet, shown in FIG. 3, having a variety of weave configurations or any combination thereof. For example, the implantable sheet material may have a solid inner configuration and a mesh outer configuration. Alternately, the implantable sheet material may have a mesh inner configuration which is tightly woven and a mesh outer configuration which is loosely woven. Other types of surgical implants may also be utilized, for example, implants made of sponge-like or gel-like material having ribs extending away from the material. While the surgical implant may be discussed as a surgical mesh, the surgical implant embodies a wide variety of configurations, as discussed above. Furthermore, the use of the term "surgical mesh" or "mesh" is not intended to limit the types of implants which may be used in the present invention.

Figure 1:
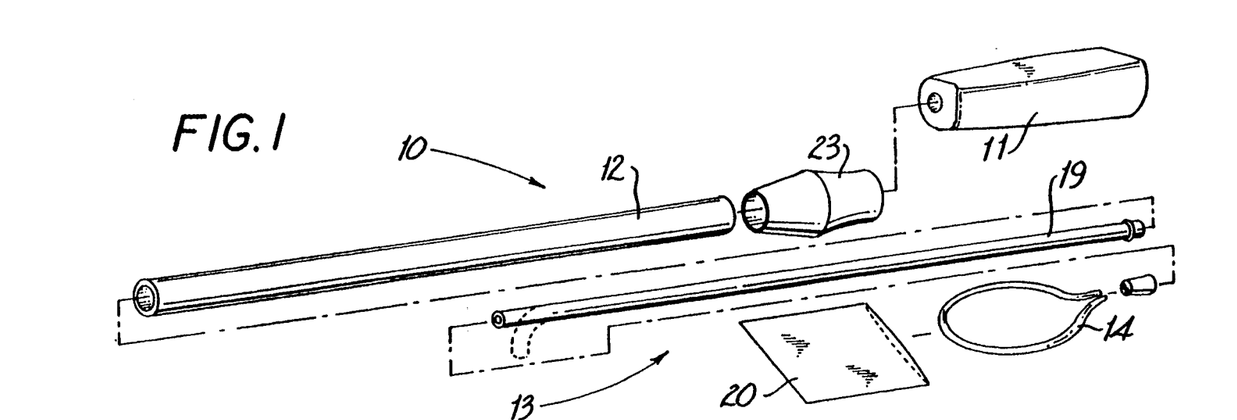
FIG. 1 is an exploded view of the preferred endoscopic implant delivery device having a solid implantable sheet material secured to the delivery device.

Referring to FIG. 1, the apparatus of the present invention, generally indicated by the numeral 10, comprises a handle portion 11, an endoscopic portion 12, a delivery device 13 coaxially positioned within the endoscopic portion having a proximal end connected to the handle portion, and a surgical implant 20 detachably secured to the delivery device.

Figure 2:
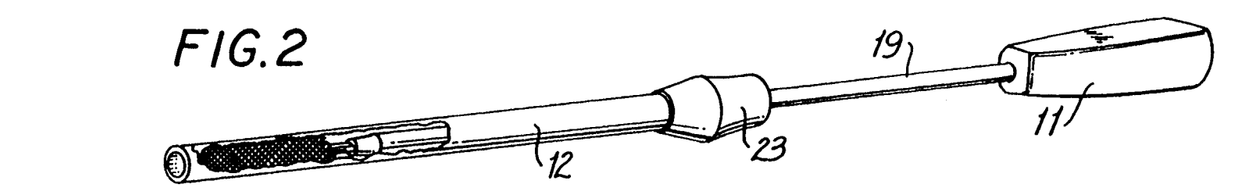
FIG. 2 is a perspective view of the preferred endoscopic implant delivery device of FIG. 1 illustrating a reciprocating tubular housing member having a surgical implant secured to a delivery device and retained therein.
Figure 3:
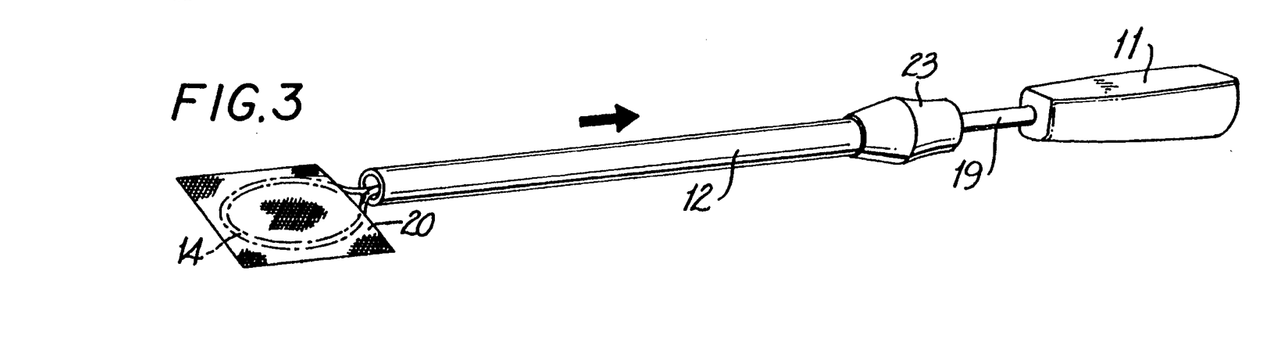
FIG. 3 is a perspective view of the preferred endoscopic implant delivery device of FIG. 1 illustrating a reciprocating tubular housing member having a mesh implantable sheet material secured to a delivery device and extended therefrom.

In a preferred embodiment shown in FIGS. 2 and 3, the endoscopic portion 12 reciprocates along the longitudinal axis of the elongated rod 19 so as to retract or extend the surgical mesh. It is also preferred that the proximal end of the endoscopic portion 12 have a gripping means secured thereto, which facilitates the reciprocating movement of the endoscopic portion 12 relative to the longitudinal axis of the elongated rod 19. As an illustrator, the surgeon may reciprocate the endoscopic portion 12 by holding the gripping means 23 in one hand and the handle assembly 11 in the other, sliding the endoscopic portion 12 along the elongated rod 19 causing the support member 14 to extend from or retract into the distal end of the endoscopic portion 12.

Preferably, the gripping means is a substantially conically shaped knob 23 as shown in FIG. 1. However, the gripping means may be in any form so long as it facilitates the reciprocal movement of the endoscopic portion 12 relative to the longitudinal axis of the elongated rod 19. For example, the gripping means may be barrel, disk or mushroom shaped member, as well as any irregular shaped member. Additionally, a grip enhancing means may be formed on or attached to the gripping means. The grip enhancing means may be in the form of protrusions extending from the gripping means or knurling formed on the gripping means, which allows the surgeon to firmly grasp the gripping means.

Figure 4:
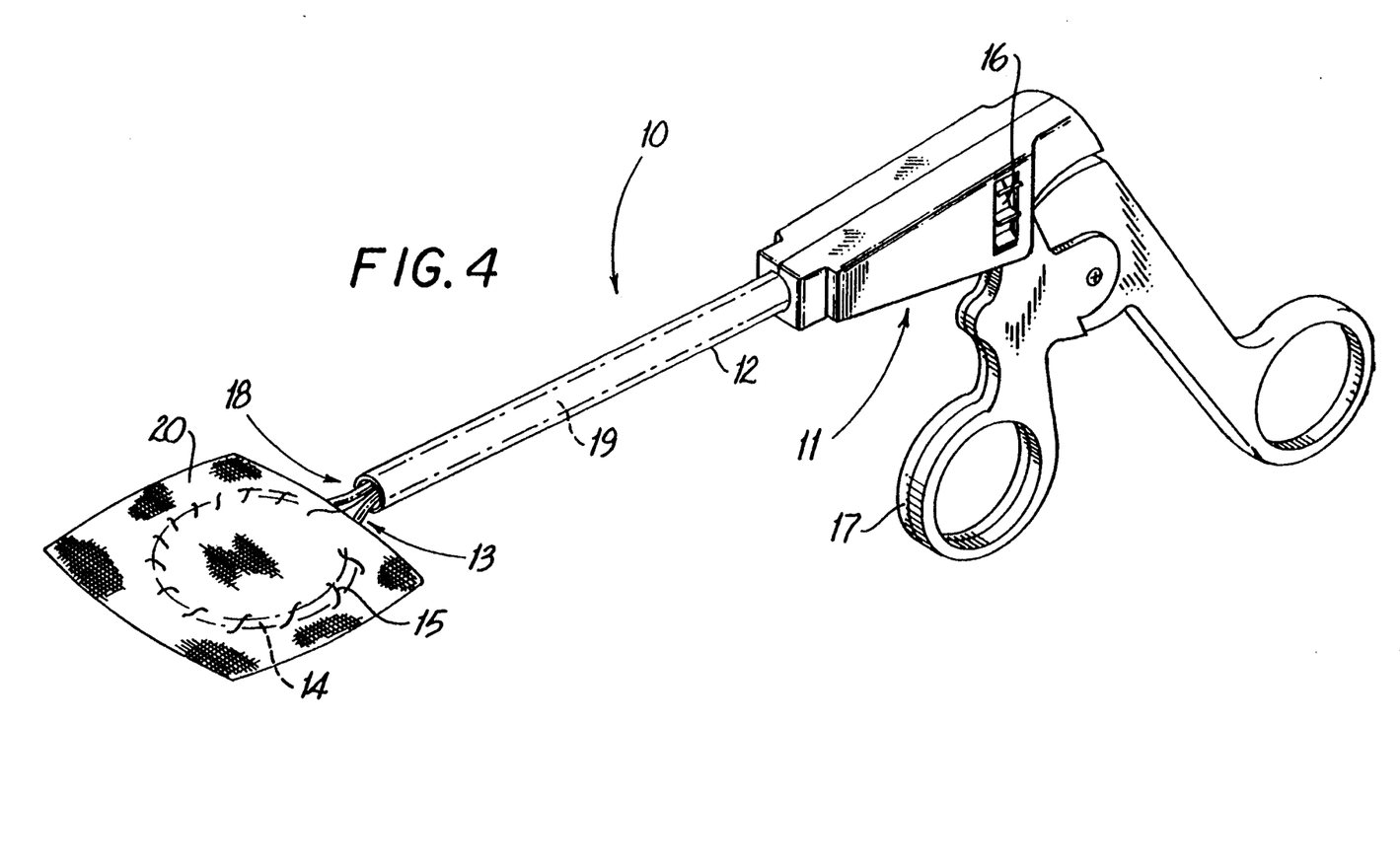
FIG. 4 is a perspective view of an endoscopic implant delivery device having an apparatus constructed according to an embodiment of the present invention operatively connected thereto.

In an alternative embodiment, the proximal end of the endoscopic portion 12 is distally connected to the handle assembly 11, as shown in FIG. 4. The elongated rod 19 is extended through the endoscopic portion 12 and operatively connected to the trigger means 17 which is pivotally secured to the handle assembly 11. Actuation of the trigger means 17, selectively causes longitudinal distal movement of the elongated rod 19 causing the support member 14 to retract into or extend from the endoscopic portion 12.

Generally, the handle portion 11 may be configured in any shape or form which can be manually manipulated during surgery. The handle portion 11 as shown in FIG. 4, may further include a rotation means 16, allowing the surgeon to rotate the support men, her 14 when positioning the implant.

The endoscopic portion 12 is generally in the form of a tubular sheath, the width and length of which depends on the type of surgery being performed. Other factors include the accessibility of the surgical site, the dimensions of the surgical implant and the delivery device being utilized. For endoscopic or laparoscopic surgical procedures the endoscopic portion 12 is configured so as to allow insertion into a cannula. For example, if a 10 mm cannula is being utilized for endoscopic positioning of the surgical implant, the diameter of the endoscopic portion 12 cannot be greater than The delivery device 13 may be adapted for use during endoscopic surgical procedures and generally includes a support member 14 which preferably forms an elongated structure 19 at its proximal end or is located at the end of an elongated rod 19 as shown in FIG. 1. The configuration of the support member 14 is adapted to facilitate detachably securing the implant thereto and to allow manipulation of the implant. The support member, for example, may be frame-like, forming a circular, oval, square, triangular, polyhedral or irregular-shaped frame. As another example, the support member may be "T", "H" or "Y" shaped. As yet another example, the support member may be solid in form such as, for example, a paddle, and may be used to press the implant against the body tissue. The support member may also be provided with eyelets through which a suture or other securing device passes after passing through or around the implant.

Figure 5:
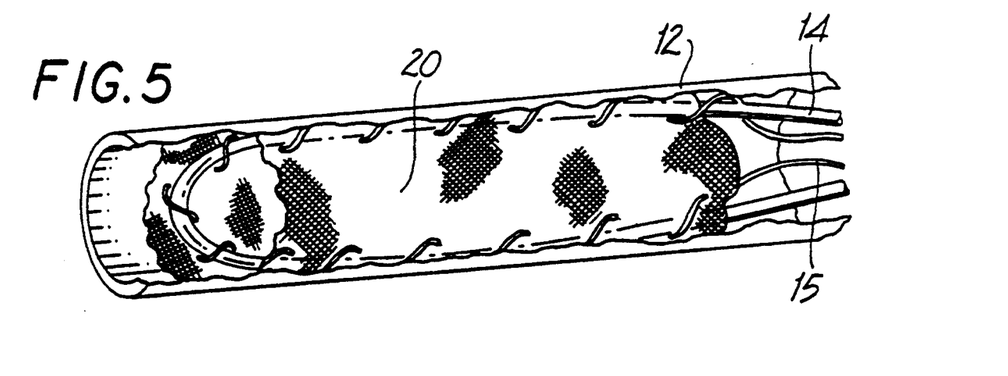
FIG. 5 is a perspective view of the distal end of the endoscopic implant delivery device constructed according to an embodiment of the present invention having a portion thereof cut away to show the internal structure.

The support member 14 of the delivery device 13 is preferably fabricated from an elastic material. As shown in FIGS. 2 and 5 the use of elastic materials allows the surgical mesh 20 and support member 14 to be compressed and retained in an endoscopic portion 12 of the apparatus 10. The elastic nature of the material will allow the support member 14 and surgical mesh 20 to assume a deployed position when extended out of the endoscopic portion 12 of the delivery device.

In one embodiment, support member 14 displays flexible, resilient memory properties. In a preferred embodiment, an articulating means is also positioned adjacent to the support member at the distal end of the elongated red. The articulating means is provided to bend or pivot the support member at an angle relative to the longitudinal axis of the elongated rod. Preferably, at least a portion of the distal end of the elongated rod adjacent to the support member 14 is fabricated from an elastic material which, in its unstressed state, assumes an angle with respect to the longitudinal axis of the endoscopic portion 12 of the apparatus 10.

Elastic materials contemplated for fabricating the support member and or the distal portion of the rod include those that have spring-like properties such that they are capable of being deformed by an applied stress and then return, or recover, to their original shape or configuration when the stress is removed. The elastic material can be either polymeric or metallic or a combination thereof, however, it is preferred that it be highly elastic. For example, such elastic materials may include silicone, polyvinyl resins, polyethylene, resilient polyacetals, resilient polyacetals, polyurethane, synthetic rubbers, teflon, tetrafluoroethylene fluorocarbon polymer, spring-tempered steel, and spring tempered stainless steel.

In addition, shape-memory alloys may be used for the elastic material. Shape-memory alloys which exhibit pseudoelastic or superelastic properties are preferred. Fundamentally, alloys which are capable of transforming between martensitic and austenitic shapes are able to exhibit shape-memory effect. The transformation between the martensitic and austenitic phases may be caused by temperature or stress.

In the case of pseudoelastic shape-memory alloys, conditions may occur where temperature is not relied on to accomplish shape change. Further, pseudoelastic alloys may be elastically deformed far beyond the elastic limits of conventional metals. Suitable shape-memory alloys are described in U.S. Pat. No. 4,665,906.

Although the preferred articulating means utilizes shape-memory alloy, other means to cause the distal end of the elongate rod adjacent to the support member to bend or pivot are envisioned including, for example, mechanical linkages.

The method utilizing the apparatus of the present invention comprises affixing a surgical implant to a delivery device, e.g., using a securing device, positioning the surgical implant and the delivery device adjacent to the body tissue, and releasing the surgical implant from the delivery device.

Figure 6:
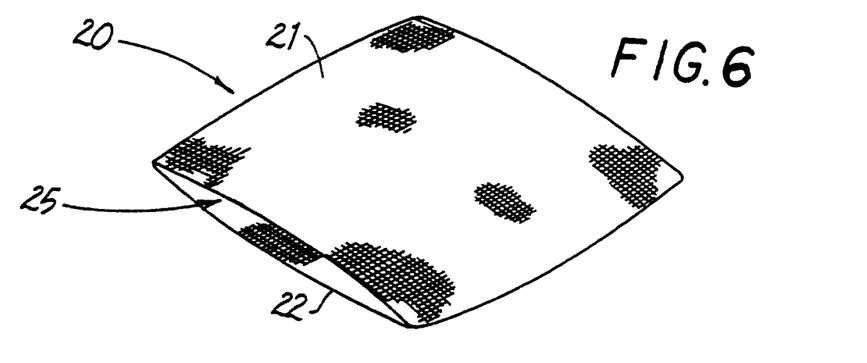
FIG. 6 is a perspective view of mesh implant having a pocket formed therein.

As discussed above the surgical implant may be fabricated from a variety of materials and configured in numerous shapes or forms. However, it is preferred that the surgical implant comprise at least two layers of implantable sheet material. In one embodiment, the surgical implant 20 is a mesh made of two layers, a first layer 21 and a second layer 22 where the layers have seams on all the sides except for one thereby forming a pocket 25, as shown in FIG. 6.

Figure 7:
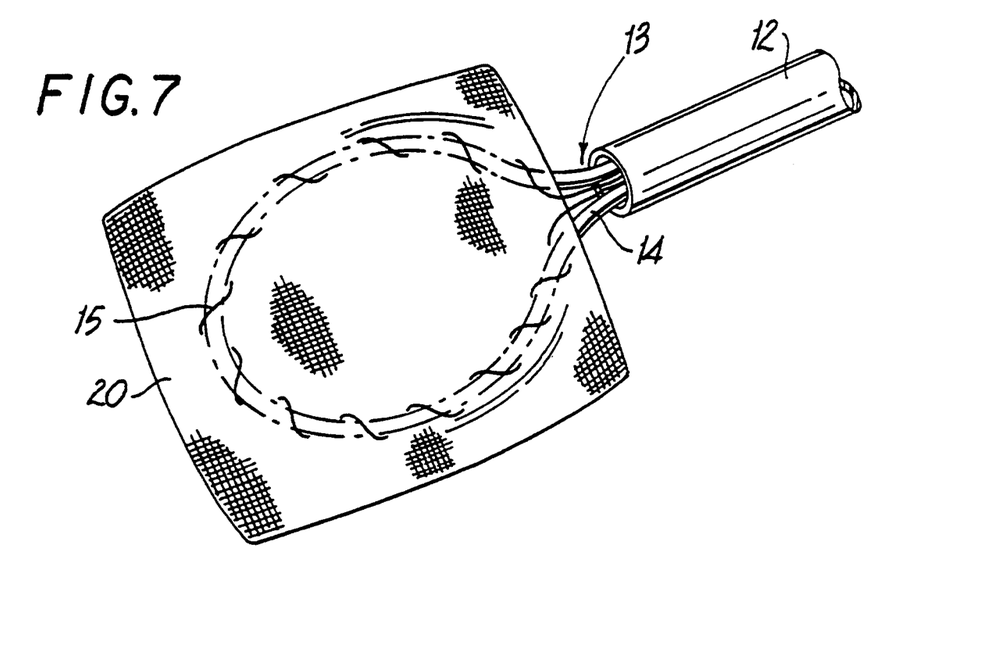
FIG. 7 is a perspective view illustrating a mesh implant having a pocket formed therein secured to a delivery device by a single suture continuously passed through the implant while wrapping around the delivery device.
Figure 8:
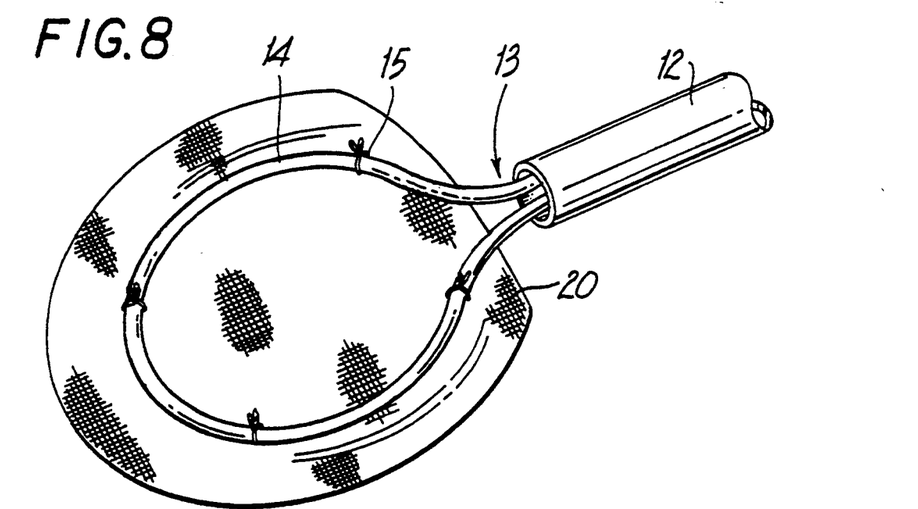
FIG. 8 is a perspective view illustrating a mesh implant secured to a delivery device by individual sutures.

The surgical implant 20 may be detachably affixed to the support member 14 in various ways. The implant 20 can be affixed by using a suture 15 or other securing device which is continuously wrapped around the support member 14 while passing it through the implant 20 as shown in FIG. 7. Alternatively, single sutures 15 may be threaded through the mesh and tied to the support member 14 as shown in FIG. 8. This technique may be repeated so as to adequately secure the surgical mesh 20 to the support member 14 for the particular application of the implant. Another embodiment includes passing a suture or sutures through apertures in the delivery device (not shown) and the surgical mesh and tie the suture or sutures, thereby securing the surgical mesh to the delivery device.

Figure 9:
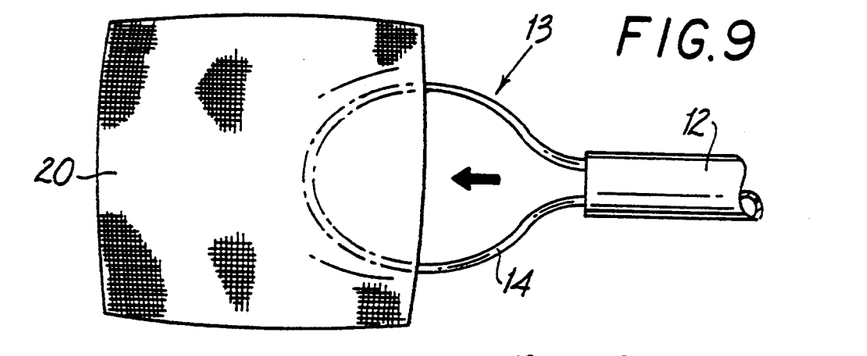
FIG. 9 is a perspective view illustrating the insertion of a delivery device into a mesh implant having a pocket formed therein.
Figure 10:
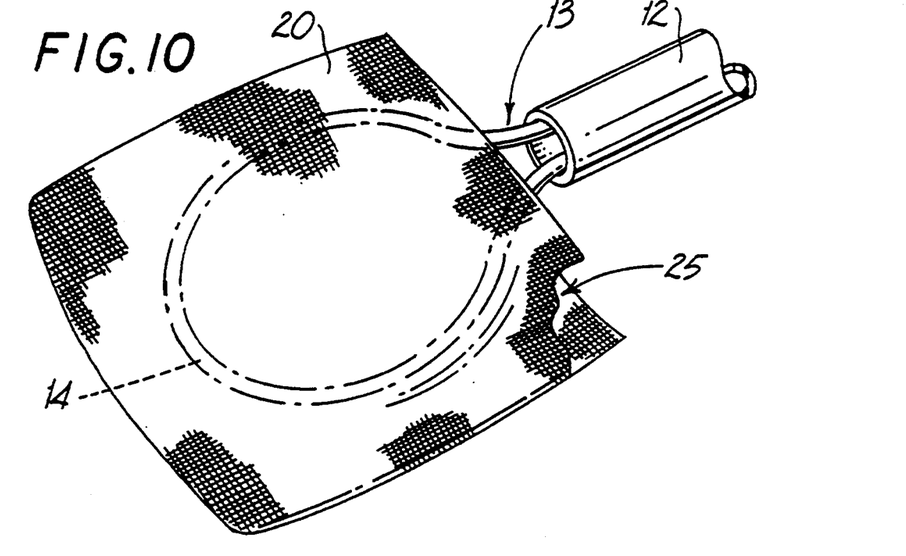
FIG. 10 is a perspective view of an alternate embodiment of the present invention illustrating a delivery device within a mesh implant having a pocket formed therein.
Figure 11:
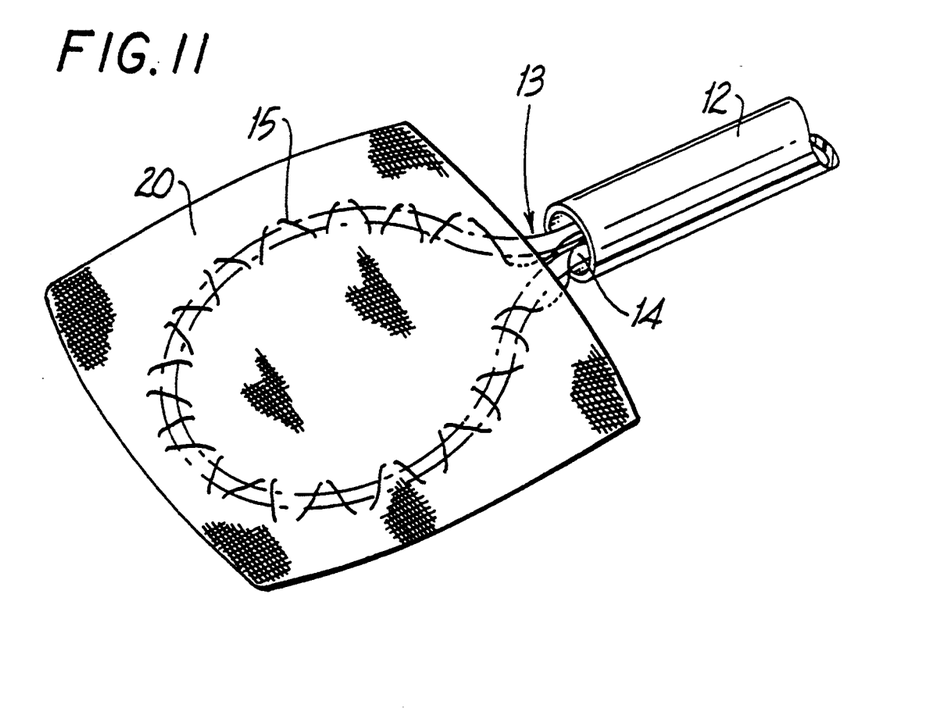
FIG. 11 is a perspective view illustrating an alternative embodiment of a mesh implant having a pocket formed therein secured to a delivery device by a single suture.
Figure 12:
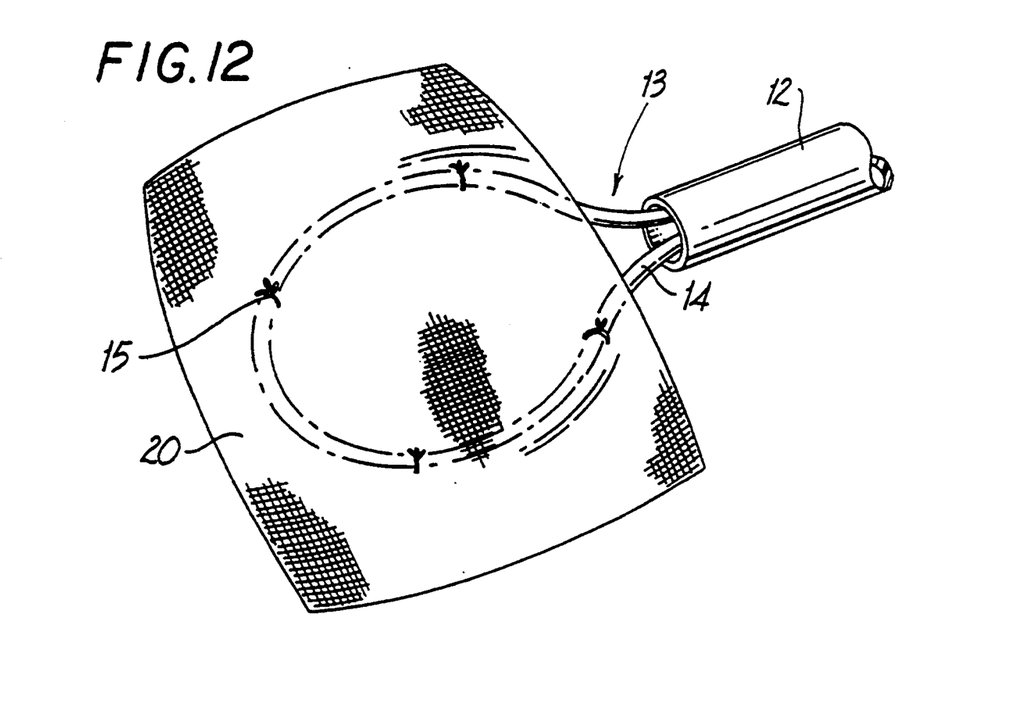
FIG. 12 is a perspective view illustrating a mesh implant having a pocket formed therein secured to a delivery device by individual sutures.

In a preferred embodiment, the support member 14 is inserted into the pocket 25 of the surgical implant 20, without further securing the support member 14 to the surgical implant 20, as shown in FIGS. 9 and 10. Alternatively, the support member 14 and surgical implant 20 may be configured so that when the support member 14 is inserted into the pocket 25 of the surgical mesh 20 the surgical mesh is frictionally, releasably secured to the support member 14. However, once inserted into the pocket 25, the support member 14 may be further secured to the mesh 20 by continuously wrapping a suture 15 or other securing device around the support member 14 while threading the suture 15 at least partially through the mesh 20 as shown in FIG. 7. In another embodiment, shown in FIG. 11, the surgical mesh may be secured to the support member 14 by threading a suture 15 through the surgical mesh on one side of the support member, rethreading the suture 15 through the surgical mesh on the same side of the support men, her 14 and then passing the suture over the support member. These steps may be repeated to sufficiently secure the surgical mesh to the support member. Additionally, the surgical mesh may be secured to the delivery device by tying individual sutures to the support member 14 and surgical mesh 20, as shown in FIG. 12. The methods disclosed for fastening the surgical implant to the delivery device are only exemplary and other techniques known by those skilled in the art may be utilized.

While describing the securing device as a suture, it should be understood that other types of yarns, threads, fibers or filaments may be used as the securing device. In addition, the securing device may be any flexible or rigid member for securing the implant to the delivery device. Preferably, the securing device is constructed to allow removal thereof to facilitate the release of the implant from the delivery device.

Once the implant is affixed to the delivery device, the surgical mesh and delivery device are positioned adjacent to the body tissue. The surgical mesh and delivery device may be positioned adjacent to the body tissue manually during conventional invasive surgical procedures. Preferably, however, for use with a hernia repair mesh an endoscopic instrument such as the apparatus of the present invention is utilized. As discussed above and referring to FIG. 1, the delivery device 13 includes a support member 14 forming a generally circular frame formed at the end of an elongated rod 19. The elongated rod 19 coaxially extends through an elongated tubular structure comprising the endoscopic portion 12 of the apparatus 10 and is connected to the handle portion 11. Actuation of the handle assembly 11 selectively causes longitudinal movement of the rod 19 causing the support member 14 to retract into or extend out of the endoscopic portion 12 of the apparatus 10. As discussed above, in one embodiment, the distal end of rod 19 is also fabricated from an elastic material which in its unstressed state assumes an angle with respect to the longitudinal axis of the endoscopic portion 12 of the apparatus 10. When the rod 19 is retracted into the tube of the endoscopic instrument, it cams against the distal end 18 of the endoscopic portion 12 and assumes a relatively straightened configuration within the endoscopic portion. When the elastic portion of the rod 19 begins to extend beyond the distal end 18 of the endoscopic portion 12 the elastic nature of this portion of the rod causes the rod to begin to bend as shown by the arrow in FIG. 13. This changes the orientation of the support member 14 and implant with respect to the longitudinal axis of the endoscopic portion 12. As a greater portion of the elastic portion extends beyond the distal end 18 of the endoscopic portion 12, the angular orientation of the support member 14 becomes greater. Ultimately, the rod 19 may extend out of the distal end 18 of the endoscopic portion 12 a distance sufficient to fully remove the stress from rod 19, whereupon the elastic material returns to its unstressed configuration, providing the maximum angle with respect to the longitudinal axis of the endoscopic portion 12 of the apparatus 10.

Figures 13, 14:
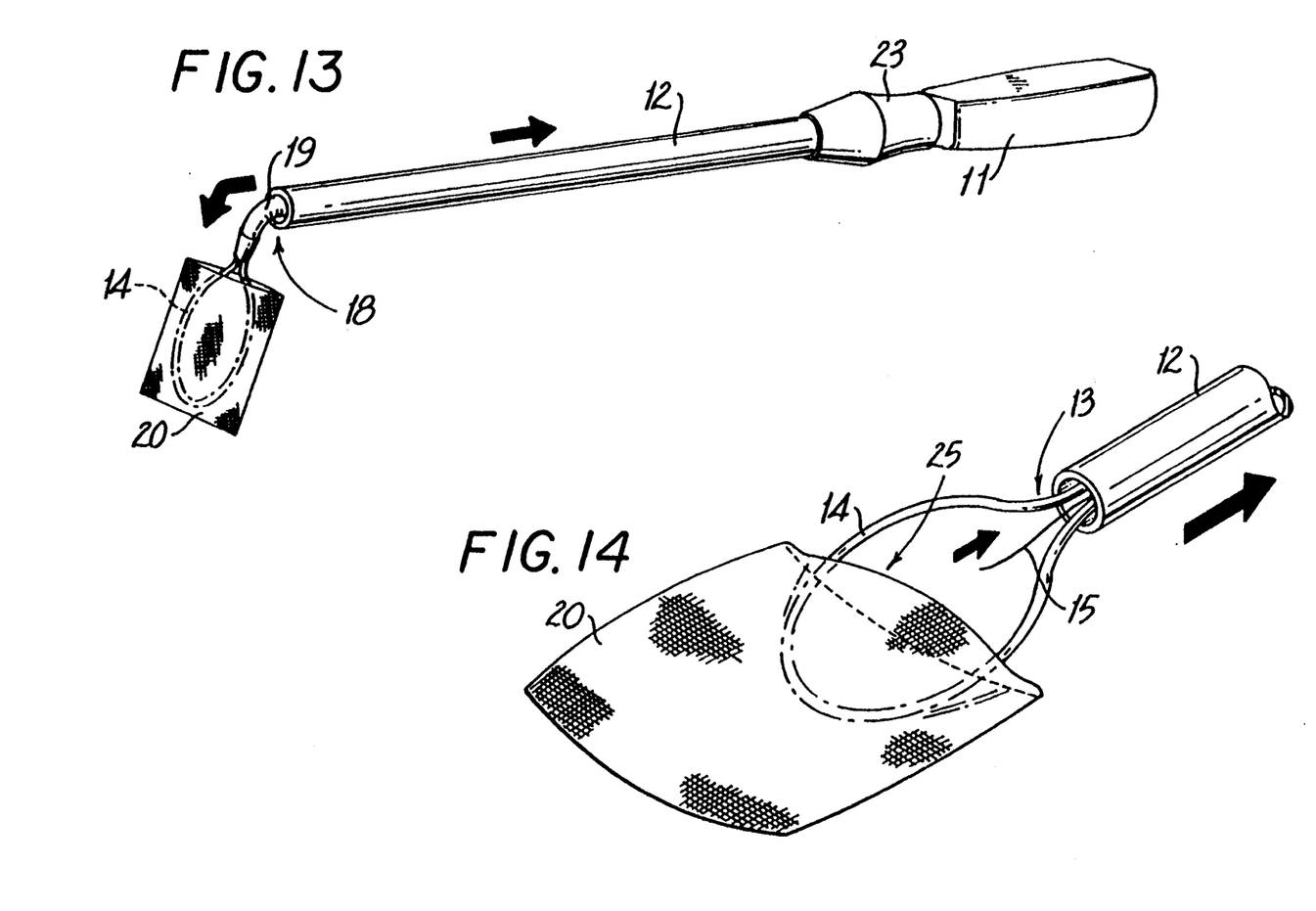
FIG. 13 is a perspective view of the distal end of an endoscopic implant delivery device with a deployed surgical implant affixed to a delivery device fabricated from an elastic material.
FIG. 14 is a perspective view illustrating the retraction cf the suture and delivery device through the distal end cf the endoscopic implant delivery device.

Employing an elastic material at the distal end of rod 19 allows delivery of the surgical mesh at a desired orientation or pressing of the mesh against the body tissue making it easier for the surgeon to fasten the surgical mesh to the tissue. It also enables the surgeon to position the delivery device and surgical mesh in areas where a straight device would Be difficult or inconvenient to use.

Once in position, the surgical implant is released from the delivery device by removing the suture from the mesh. In the case of the preferred embodiment, the support member 14 is simply retracted from the mesh pocket 25, as shown in FIG. 14. When a continuously threaded suture or sutures are utilized to secure the support member to the surgical mesh, removal of the suture 15 or sutures may be accomplished by pulling them from the implant. Alternatively, as illustrated in FIG. 14, the suture 15 may extend into the endoscopic portion 12 of the instrument and either exit the instrument at the handle assembly 11 to allow manual removal of the suture, or alternatively, be operatively connected to the handle assembly where a trigger or other actuating structure (not shown) causes withdrawal of the suture. When individual sutures are tied to the delivery device, the surgeon may remove the suture 15 or other securing device by manually cutting the suture or securing device using conventional cutting devices at one or more points as required to release the mesh from the delivery device. Once the securing device is removed, the mesh may be held in place by the delivery device pressing it against the body tissue. Alternatively, the mesh may be secured to the body tissue prior to removal of the securing device by fastening means, such as, sutures, clips and/or staples.

It will be understood that various modifications can be made to the embodiments of the present invention herein disclosed without departing from the spirit and scope thereof. For example, various sizes of the delivery device and endoscopic instrument are contemplated, as well as various types of construction materials. Also, various modifications may be made in the configuration of the parts. Therefore, the above description should not be construed as limiting the invention but merely as exemplifications of Preferred embodiments thereof. Those skilled in the art will envision other modifications within the scope and spirit of the present invention as defined by the claims appended hereto.

What is claimed is:

1. An apparatus for positioning surgical implants adjacent to body tissue, comprising:
    an outer tube having a proximal end, a distal end and a longitudinal axis;
    an inner rod at least partially disposed within said outer tube and slidable along said longitudinal axis, said inner rod having proximal and distal end portions, said inner rod distal end portion further comprising articulating means for pivoting at an angle with respect to said longitudinal axis;
    a looped support member having first and second ed portions fixedly secured to said distal end portion of said inner rod; and
    a surgical implant releasably secured to said looped support member.

2. An apparatus according to claim 1, wherein said surgical implant is at least partially fabricated from surgical mesh.

3. An apparatus according to claim 1, wherein said articulating means comprises an elastic material having an unstressed configuration at an angle with respect to said longitudinal axis.

4. An apparatus according to claim 3, wherein said elastic material is a shape-memory alloy.

5. An apparatus according to claim 3, wherein said angle is at least 90°.

6. An apparatus according to claim 1, wherein said surgical implant is at least partially releasably secured by a suture.

7. Apparatus for positioning surgical implants adjacent to body tissue, comprising:

a delivery device having a support member positioned at the distal end of an elongated rod;

an implantable sheet material releasably secured to said support member by securing means such that said implantable sheet material is manipulable for subsequent securement to said body tissue by fastening means;

an elongated tube for at least partially enclosing said support member, said elongated rod and said implantable sheet material;

a handle portion proximally extending from said elongated tube;

trigger means operatively connected to said elongated rod for alternately moving said implantable sheet material between retracted and extended positions; and rotation means for rotating said elongated rod around its longitudinal axis.

8. An apparatus for positioning surgical implants adjacent to body tissue, comprising:

an outer tube having a proximal end, a distal end and a longitudinal axis;

an inner rod at least partially disposed within said outer tube and slidable along said longitudinal axis, said inner rod having proximal and distal end portions;

a looped support member having first and second ends fixedly secured to said distal end portion of said inner rod; and a surgical implant having a first layer coupled to a second layer such that a pocket is formed therebetween, said pocket being adapted to slidably receive said looped support member, wherein said implant first and second layers are substantially the same dimension.

9. An apparatus according to claim 8, wherein said surgical implant is at least partially fabricated from surgical mesh.

10. An apparatus according to claim 8, wherein said surgical implant is at least partially secured to said looped support member by at least one suture.

11. An apparatus according to claim 10, wherein said suture is at least partially disposed in said outer tube.

12. An apparatus for positioning surgical implants to body tissue, comprising:

an outer tube having a proximal end, a distal end and a longitudinal axis;

an inner rod at least partially disposed within said outer tube and slidable along said longitudinal axis, said inner rod having proximal and distal end portions;

a looped support member at least partially secured to said distal end portion of said inner rod; and a surgical implant at least partially fabricated from surgical mesh releasably secured to said looped support member by at least one suture, wherein said surgical implant comprises a first substantially rectangular layer at least partially coupled on three sides to a second substantially rectangular layer such that a pocket is formed therebetween, said pocket being adapted to slidably receive said support member wherein said implant first and second layers are of substantially the same dimension.

* * * * *